United States Patent [19]

Fujikura et al.

[11] Patent Number: 4,604,488

[45] Date of Patent: Aug. 5, 1986

[54] CYCLOHEXANOL DERIVATIVES AND FRAGRANCE COMPOSITIONS CONTAINING THE SAME

[75] Inventors: Yoshiaki Fujikura, Utsunomiya; Yasushi Kajihara, Ichikaimachi; Naotake Takaishi; Yoshiaki Inamoto, both of Utsunomiya; Akio Kimura, Wakayama; Motoki Nakajima, Miyashiromachi; Norioki Miyamoto, Yotsukaido, all of Japan

[73] Assignee: Kao Corporation, Tokyo, Japan

[21] Appl. No.: 563,972

[22] Filed: Dec. 21, 1983

[30] Foreign Application Priority Data

Dec. 22, 1982 [JP] Japan ................................ 57-225264

[51] Int. Cl.⁴ ............................................. C07C 35/22
[52] U.S. Cl. ................................... 568/820; 568/819; 568/830; 252/522 R
[58] Field of Search ............... 568/734, 830, 832, 819, 568/820, 821, 822; 252/522

[56] References Cited

U.S. PATENT DOCUMENTS

| | | | |
|---|---|---|---|
| 3,692,844 | 9/1972 | Hollis et al. | 568/734 |
| 3,878,254 | 4/1975 | Gazave | 568/734 |
| 4,014,944 | 3/1977 | Hall et al. | 568/820 |
| 4,061,686 | 12/1977 | Hall et al. | 568/734 |
| 4,067,899 | 1/1978 | Mardiguian | 568/734 |
| 4,070,402 | 1/1978 | Karl et al. | 568/734 |
| 4,112,000 | 9/1978 | Mardiguian | 568/734 |
| 4,239,920 | 12/1980 | Conte | 568/734 |
| 4,301,306 | 11/1981 | Layer | 568/734 |

FOREIGN PATENT DOCUMENTS

| | | | |
|---|---|---|---|
| 3346213 | 7/1984 | Fed. Rep. of Germany | 568/820 |
| 0115360 | 9/1979 | Japan | 568/734 |
| 159860 | 1/1964 | U.S.S.R. | 568/734 |

OTHER PUBLICATIONS

Vasil'eva, "Chemical Abstracts" vol. 84, (1976) p. 418, 30579x.

Fragrance Guide Masculine Notes, Fragrances on the International Market, H & R Edition (1985) published by Johnson Publication Limited, London.

*Primary Examiner*—Werren B. Lone
*Attorney, Agent, or Firm*—Oblon, Fisher, Spivak, McClelland & Maier

[57] ABSTRACT

Fragrant cyclohexanol derivatives are produced by condensing 2-ethylidene-5-norbornene with a phenol compound, in the presence of a Friedel-Crafts catalyst; and hydrogenating the condensation product in the presence of a metal catalyst.

The compounds so produced have a green-floral odor and are advantageously used in soaps, detergents, shampoos, hair rinse, cosmetics, colognes and perfumes.

15 Claims, 2 Drawing Figures

CYCLOHEXANOL DERIVATIVES AND FRAGRANCE COMPOSITIONS CONTAINING THE SAME

BACKGROUND OF THE INVENTION

1. Field of the Invention

The present invention relates to cyclohexanol derivatives and fragrance compositions containing the same.

2. Description of the Prior Art

It is known that hydrogenated catecholcamphene adducts obtained by the hydrogenation of an adduct of camphene with catechol have a sandal odor. (Japan Patent Application Laid-Open No. 106,853/1977 and No. 118,507/1982). It is also known that condensation of 2-ethylidene-5-norbornene ("EBH") with phenol in the presence of a cation exchange resin gives a 1:1 condensation product. (Chemical Abstracts, Vol. 84, 30579x (1974); Neft. Gaz, page 128 (1974)).

While fragrant substances are known which have a green-floral type odor, many of the fragrance materials belonging to the green-floral odor type have an aldehyde group as a functional group. (Perfumer and Florist, 5 (6), 1 (1980) and ibid., 6 (1), 1 (1981)). Unfortunately, the aldehyde group is known to be easily oxidizable and notoriously susceptible to attack by acids and alkalis. Hence, fragrant substances bearing an aldehyde group tend to be chemically labile or unstable.

Additionally, many of the fragrant substances having a green-floral type odor have a relatively simple chemical structure and, hence, a low molecular weight, which results in the non-persistence of the odor. Hence, a need continues to exist for a fragrant substance or fragrance composition which has a green-floral type odor and which is chemically stable. Moreover, a need also continues to exist for such compositions or substances whose green-floral type odor is persistent.

SUMMARY OF THE INVENTION

Accordingly, it is an object of the present invention to provide a fragrance composition having a green-floral type odor which is chemically stable and not easily oxidizable or susceptible to attack by acids or alkalis.

Moreover, it is also an object of the present invention to provide a fragrance composition having a green-floral type odor which is compatibile with, and can be incorporated with, soaps, detergents, shampoos, hair rinses and various types of comestics, cologne and perfume.

According to the present invention, the foregoing and other objects are attained by providing a fragrant mixture comprising of least one cyclohexanol derivative having the formula:

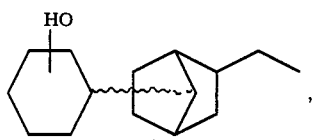

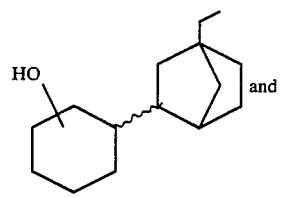

and

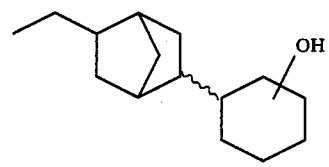

DETAILED DESCRIPTION OF THE PREFERRED EMBODIMENTS

Figure 1:
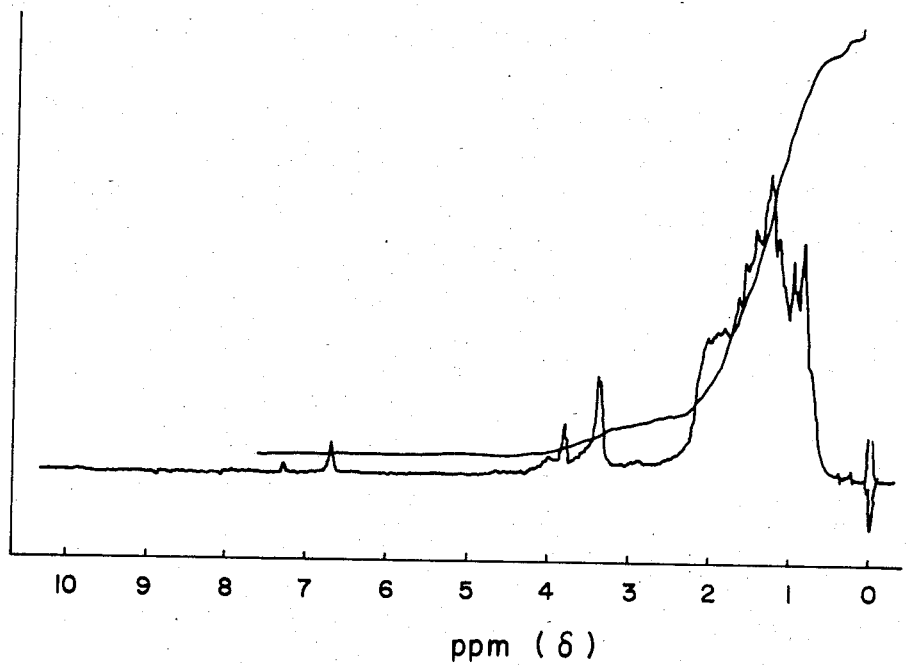
FIG. 1 shows the nuclear magnetic resonance (NMR) spectrum of the cyclohexanol derivative product according to the present invention.

According to the present invention, cyclohexanol derivatives are now available which can be used advantageously in the preparation of fragrance compositions. In particular, the cyclohexanol derivatives of the present invention are prepared by condensing 2-ethylidene-5-norbornene ("EBH") having the formula (I):

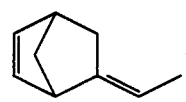 (I)

with a phenol compound of the formula (II):

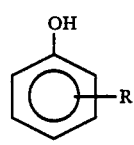 (II)

wherein R is a hydrogen atom or a hydroxyl or lower alkoxy group, in the presence of a Friedel-Crafts catalyst; and hydrogenating the EBH-phenol compound adduct.

When the EBH-phenol compound adducts are hydrogenated, the cyclohexanol derivatives of the present invention are produced. These derivatives have a green-floral type odor.

In the production of the cyclohexanol derivatives according to the invention, EBH is first condensed with a phenol in the presence of a Friedel-Crafts catalyst. Examples of the phenol compounds to be used are phenol (in formula (II), R=H), catechol (R=OH), and guaiacol, guethol (o-ethoxyphenol) and the like (R=lower alkoxy having 1 to 4 carbon atoms). As the Friedel-Crafts catalyst, there may be used those acid cataylsts which are in general use, such as cation exchange resins, boron trifluoride, boron trifluoride etherate, boron trifluoride-acetic acid, boron trifluoride-phosphoric acid, boron trifluoride-methanol, celite, acid clay, sulfuric acid, aluminum trichloride, zinc chloride, stannic chloride and ferric chloride (G. A Olah: Friedel-Crafts Chemistry, 1973).

The reaction is carried out by adding EBH dropwise to a solution of the phenol compound and Friedel-Crafts catalyst in an adequate solvent. The Friedel-Crafts catalyst is used in an amount of about 0.01 to 40 percent by weight based on the phenol compound. The molar ratio between the phenol and EBH is about 1:1 to 20:1, preferably about 1.5:1 to 10:1.

As the solvent, a halogenated hydrocarbon, such as methylene chloride, chloroform or carbon tetrachloride, is preferred. While the reaction temperature depends on the catalyst species used, the reaction is generally carried out at about −10° C. to 250° C. For instance, when boron trifluoride-acetic acid is used, temperatures of about −10° C. to 180° C., especially room temperature to 160° C., are preferred, whereas when sulfuric acid, celite or acid clay is used, temperatures of about 50° C. to 250° C. are preferred. The reaction time also depends on the catalyst species used. Generally, the reaction is complete in 1 to 10 hours.

The thus-obtained main product is considered, based on the $^1$-NMR data obtained, to be composed mainly of the following two compounds (III) and (IV):

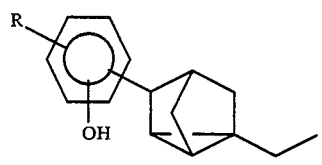
(III)

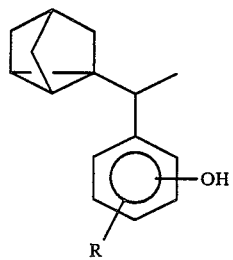
(IV)

wherein R is defined above.

However, the condensation reaction between EBH and anisole as depicted below under "Alternative Synthesis 1" revealed that the EBH-phenol compound adduct is a compound of formula (III) (cf. Referential Example 1).

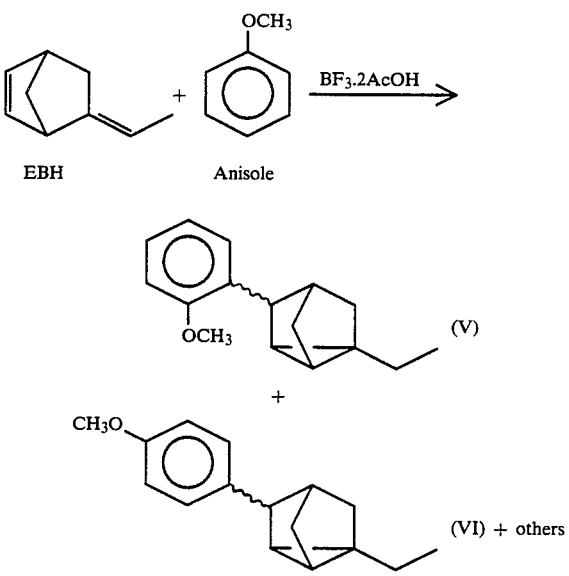

Alternative Synthesis 1

The fact that various spectral data for the compounds (V) and (VI) obtained in the above confirmation reaction were in agreement with those for the compounds (VII) and (IX) obtained by an alternative method (Alternative Synthesis 2) proved that the structure of compounds (V) and (VI) are shown above (cf. Referential Examples 2-5).

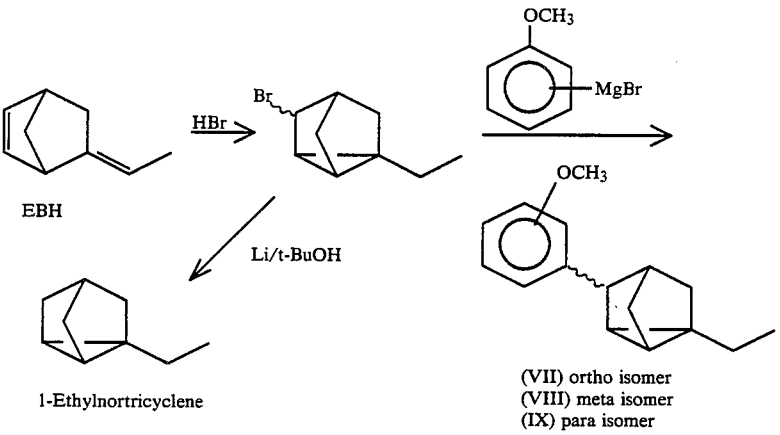

Alternative Synthesis 2

The EBH-phenol compound adduct is then hydrogenated. It is necessary to perform this hydrogenation under such conditions that (1) hydrogenation of the aromatic ring, (2) elimination of other substituents than one phenolic hydroxyl group and (3) cleavage of the cyclopropane ring can take place.

Such hydrogenation is effected by using a metal catalyst such as Raney nickel, nickel-on-diatomaceous earth, Raney cobalt, platinum, rhodium, ruthenium, ruthenium-on-active carbon or palladium. There is no particular limit to the amount of the catalyst. Preferably, however, the catalyst is used in the amount of about 0.1 to 20 percent by weight based on the above-mentioned EBH-phenol compound adduct. For instance, good results can be obtained by using about 1-20 percent by weight of Raney nickel or about 0.1-5 percent by weight of ruthenium-on-activated carbon, each based on said adduct. The hydrogenation is carried out generally at a hydrogen pressure between about 1 atm. pressure and about 200 kg/cm$^2$, preferably at about 10-150 Kg/cm$^2$, more preferably at about 50-100 Kg/cm$^2$, and at a temperature of about 100° C. to 300° C., preferably about 130°-230° C. At temperatures below 100° C., the rate of reaction becomes slow, whereas, at temperatures exceeding 300° C., the formation or hydrocarbons and other byproducts unfavorably increases.

This hydrogenation reaction can be carried out either in the presence or in the absence of a solvent. However, the use of a lower alcohol such as methanol, ethanol or isopropyl alcohol, or a saturated hydrocarbon such as hexane or cyclohexane, for instance, is preferred. When a nickel catalyst is used, an alkaline substance or a neutral or acidic inorganic dehydrating agent may be added.

The cyclohexanol derivatives obtainable in the above manner have the following physical characteristics:
Appearance: Colorless viscous liquid;
Boiling point: 95°-125° C./0.1 mmHg;
Elemental analysis: C 78-82%; H 8-12%; O 7-14%.

With respect to the molecular structure of the formed cyclohexanol derivative, compounds having the following three structures are formed depending on the mode of cleavage of the cyclopropane ring in the above hydrogenation reaction:

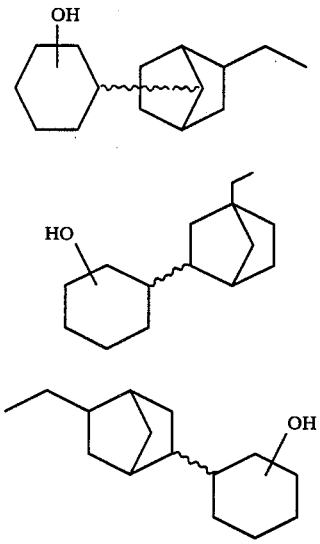

Moreover, with respect to the compounds having the formulas (X) to (XII), there are a number of possible isomers depending on the configuration of the cyclohexyl group and the configuration of the ethyl group. The use of gas chromatography with a capillary column has confirmed that the cyclohexanol derivative according to the present invention is a mixture of various isomers.

The cyclohexanol derivative product according to the present invention has a green-floral type odor and has the following advantageous features:

(1) Generally, many of the fragrance materials belonging to the green-floral odor type have an aldehyde group as the functional group (*Perfumer and Florist*, 5 (6), 1 (1980) and ibid., 6 (1), 1 (1981)) and the aldehyde group is easily oxidizable and susceptible to acids and alkalis, and therefore an instability problem is encountered. On the other hand, the compound according to the present invention is an alcohol free from such instability.

(2) Many of the materials having a green-floral type odor have relatively simple chemical structures and are low in molecular weight, so that their odor is not persistent. On the other hand, the compounds according to the present invention contain 15 carbon atoms and have rather complicated ring structures, so that their odor remains persistent for a very long time. For instance, the odor is retainable for more than one month on filter paper.

Accordingly, the cyclohexanol derivatives according to the present invention can be incorporated, in the form of a fragrance composition, into various products, such as soap, detergent, shampoo, hair rinse, various types of cosmetics, cologne and perfume.

The present invention will be further illustrated by certain examples and references which are provided for purposes of illustration only and are not intended to limit the present invention.

EXAMPLE 1

(i) A solution composed of 372 g (3.0 moles) of guaiacol and 15 g of boron trifluoride-acetic acid was heated to 50° C. while stirring. Thereto was added dropwise 120 g (1 mole) of EBH over 2.5 hours, while cooling in an adequate manner so as to prevent the temperature from rising with the progress of the exothermic reaction and to maintain the reaction temperature at 50° C. After completion of the dropwise addition, stirring was continued at the same temperature for one additional hour. Thereafter, the reaction mixture was cooled to room temperature, followed by addition of 36 g of 15% aqueous sodium hydroxide. The aqueous layer was removed, and the organic layer was distilled under reduced pressure, whereby the unreacted starting guaiacol was first distilled off. Continued distillation under reduced pressure gave a product.
Boiling point: 155°-170° C./0.1 mmHg;
Yield: 34.7 g(14.2%).

Gas chromatography-mass spectrometry of the product using Carbowax 20M (50 m capillary column) gave a parent peak at m/e=244, indicating that the product was a 1:1 adduct of guaiacol with EBH.

$^1$H-NMR (CDCl$_3$, TMS internal standard, δ): 6.5 (complicated multiplet, aromatic ring hydrogens, 3H), 5.3 (phenol —OH), 3.7 (3H, —OCH$_3$), 3.3-1.8 (complicated multiplet, 13H);

IR (liquid film, cm$^{-1}$): 3550, 3450, 3050, 2960, 2875, 1590, 1515, 1490, 1465, 1380, 1350, 1320, 1270, 1200, 1130, 1100, 1080, 1060, 1040, 960, 870, 850, 820, 795, 780, 760, 735.

(ii) A 100-ml autoclave was charged with 20 g of the condensation product obtained in (i), 10 g of isopropyl alcohol and 2 g of Raney nickel, and hydrogenation was conducted at a reaction temperature of 170°-180° C. and a hydrogen pressure of 50 Kg/cm$^2$ (gauge) with stirring for 3.5 hours. The product was rectified to give 12.4 g (68%) of a viscous fraction boiling at 105°-120° C./0.35 mmHg. This fraction had a strong odor of the green-floral type. Gas chromatography-mass spectrometry of the product using Carbowax 20M (50 m capillary column) revealed that 67.4% of the product was accounted for by cyclohexanol derivatives. The results of analyses are shown below:

GC-MS:

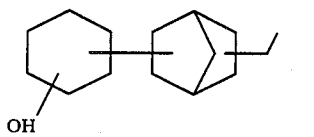

m/e = 222(36.7%)

(The position and configuration for each of the ethyl, cyclohexyl and hydroxyl groups unknown.)

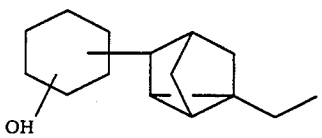

m/e = 220(30.7%)

(The position and configuration for each of the ethyl, cyclohexyl and hydroxyl groups unknown.)

Unhydrogenated material m/e=244 (20.3%) Others (12.3%)

Figure 2:
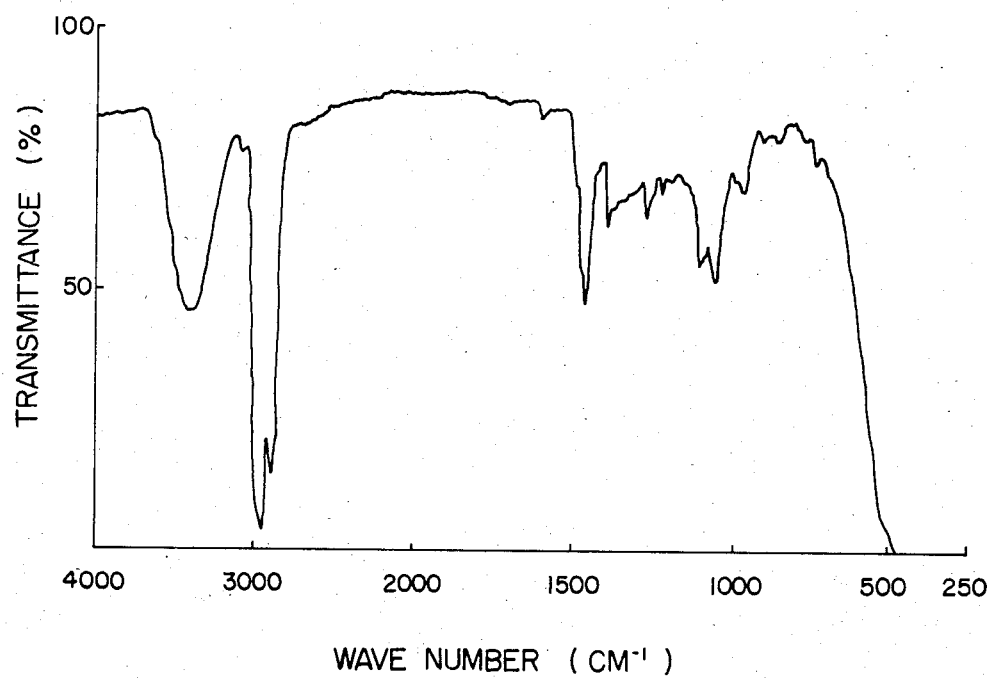
FIG. 2 shows the infra-red (IR) absorption spectrum of the cyclohexanol derivative product according to the present invention.

$^1$H-NMR (CDCl$_3$, TMS internal standard, δ): FIG. 1 6.5 (unhydrogenated aromatic ring), 3.7 (—OCH$_3$) (unreacted methoxy group), 3.3—0.2 (complicated multiplet);

IR (liquid film, cm$^{-1}$): FIG. 2 3350, 2940, 2860, 1590, 1490, 1460, 1380, 1270, 1100, 1050, 970, 780, 730,

EXAMPLE 2

(i) A solution composed of 744 g (6 moles) of guaiacol and 0.26 g of concentrated sulfuric acid was heated to 150° C. while stirring. Thereto was added dropwise 240 g (2 moles) of EBH over 2.5 hours. After completion of the dropwise addition, the temperature was raised to 200° C. and stirring was continued at that temperature for 6 hours. Thereafter, the reaction mixture was cooled to room temperature, and 1.42 g of 15% sodium hydroxide was added. After removal of the aqueous layer, the organic layer was distilled under reduced pressure, whereby the unreacted starting guaiacol was first distilled off. Continued distillation gave a product.

Boiling point: 130°-152° C./0.1 mmHg,
Yield: 152.9 g (62.7%)

Gas chromatography-mass spectrometry of the product using a capillary column confirmed that the product contained the same compounds as those contained in the product of Example 1-(i), although two products differed in content of each constituent.

EXAMPLE 3

A 100-ml autoclave was charged with 20 g of the guaiacol-EBH adduct obtained in Example 1-(i), 10 g of ethanol and 1 g of 5% ruthenium-on-activated carbon, and hydrogenation was conducted at a reaction temperature of 150° C. and a hydrogen pressure of 100 Kg/cm$^2$ while stirring for 4 hours. Rectification of the product gave 12.9 g (71% yield) of a viscous fraction boiling at 99°-115° C./0.15 mmHg. This fraction had a strong odor of the same green-floral type as the fraction obtained in Example 1-(ii) and its physical characteristics data were almost the same as those for the fraction obtained in Example 1.

EXAMPLE 4

Rosy fragrance composition:

| | |
|---|---|
| Geraniol | 130 (g) |
| Citronellol | 70 |
| Phenylethyl alcohol | 593 |
| Nerol | 50 |
| Geranium oil | 20 |
| Palmorosa oil | 20 |
| Benzyl acetate | 20 |
| Hydroxycitronellal | 40 |
| Linalool | 25 |
| Octanol | 1 |
| Octanal | 1 |
| Geranyl acetate | 10 |
| Phenylethyl acetate | 10 |
| Citronellyl acetate | 10 |
| | 1,000 |

To 1,000 g of the above fragrance composition was added 50 g of the cyclohexanol derivative obtained in Example 1-(ii) to give a novel, fresh and rosy, retainable fragrance composition.

EXAMPLE 5

Fragrance composition for shampoo:

| | |
|---|---|
| Linalool | 50 (g) |
| Jasmine absolute oil | 20 |
| Phenylethyl alcohol | 150 |
| Rhodinol | 150 |
| Rose absolute oil | 10 |
| Hydroxycitronellal | 300 |
| Indole | 2 |
| 4-(4-Hydroxy-4-methylpentyl)-3-cyclohexene-1-carboxaldehyde | 78 |
| α-Hexylcinnamic aldehyde | 150 |
| Cyclamen aldehyde | 40 |
| Sandalwood oil | 50 |
| | 1,000 |

To 1,000 g of the above fragrance composition was added 50 g of the cyclohexanol derivative obtained in Example 1-(ii) to give a novel, fresh and retainable fragrance composition having a lily-of-the-valley-like odor.

EXAMPLE 6

Fragrance composition for soap:

| | |
|---|---|
| Citronellol | 100 |
| Dimethylphenylethylcarbinol | 100 |
| Geraniol | 100 |
| α-Hyxylcinnamic aldehyde | 150 |
| Hydroxycitronellal | 200 |
| Phenylethyl alcoohol | 250 |
| 1,3,4,6,7,8-Hexahydro-4,6,6,7,8,8-hexamethylcyclopenta-γ-2-benzopyran | 20 |
| p-tert-Butylcyclohexyl acetate | 50 |
| Acetylcedrene | 30 |
| | 1,000 |

To 1,000 g of the above fragrance composition was added 50 g of the cyclohexanol derivative obtained in Example 1-(ii), whereby a novel, fresh fragrance composition very well retainable on the skin was obtained.

Referential Example 1

Condensation product from EBH and anisole:

Using 486 g (4.50 moles) of anisole, 180 g (1.50 moles) of EBH and 19 g of boron trifluoride-acetic acid, the procedure of Example 1-(i) was followed. Distillation gave a product.

Boiling point: 130°–160° C./0.4 mmHg;
Yield: 101 g (29.5%);
GC-MS (Carbowax-20M, 50 m capillary column): m/e=228.

The retention time data obtained by GC using a capillary column (Thermon 600TK, 50 m) indicated that the product contained compounds (V) and (VI) as main products in proportions of 29.6% and 37.0%, respectively. These compounds were isolated by gas chromatography (Silicone SE-30, 2 m) and subjected to $^{13}$C-NMR spectrometry. The NMR data obtained for said compounds were in agreement with those for separately synthesized authentic samples (Referential Examples 3 and 4) of the main products (VII) and (IX), respectively. Gas chromatography-mass spectrometry using a capillary column revealed that the above condensation product contained isomers of the separately synthesized authentic samples (VII) and (IX), namely isomers differing in configuration of the aromatic ring, in a total amount of 7.7%.

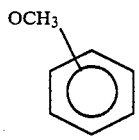

(V), (VII): ortho isomer
(VIII): meta isomer
(VI), (IX): para isomer

Referential Example 2

1-Ethyl-3-bromonortricyclene(1-ethyl-3-bromotricyclo[2,2,1,0$^{2,6}$]heptane):

To 120 g (1.0 mole) of EBH was added 172 g (1.0 mole) of 47% hydrobromic acid. The mixture was stirred vigorously at room temperature for 24 hours and, thereafter, extracted with 300 ml of ether and further with two 100-ml portions of ether. The combined extract was washed with a 50-ml portions of saturated aqueous sodium chloride, and dried over magnesium sulfate. Unreacted EBH (282 g) was recovered by distillation under reduced pressure. Continued distillation gave a product. This product was composed of two isomers differing in configuration of bromine (72% and 28%).

Boiling point: 88.0°–90.0° C./1.5 mmHg;
Yield: 127.6 g (83% based on the reacted EBH).
$^1$H-NMR (CDCl$_3$, TMS internal standard, δ): 4.0 (1H, CH-Br), 2.2−1.2 (complicated multiplet, 9H), 0.9 (3H, —CH$_3$).
IR (liquid film, cm$^{-1}$): 3060, 2960, 2875, 1460, 1220, 895 800, 730.
$^{13}$C-NMR (CDCl$_3$, δ):

For the major one (72%) of the two compounds produced (which presumably has the following configuration):

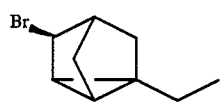

11.8(q), 17.7(d), 22.6(t), 24.0(d), 28.7(s), 32.0(t), 34.7(t), 39.5(d), 57.6(d)

For the minor one (28%) of the two compounds produced (which presumably has the following configuration):

Two peaks were unidentifiable as they overlapped with the peaks of the major product.

12.2(q), 20.0(d), 22.1(t), 26.5(s), 32.6(t), 34.0(t), 58.5(d)

To confirm that the thus-obtained bromide has the carbon skeleton shown above, the bromide was subjected to debromination. That is, 10.1 g (50 millimoles) of the above bromide, 20 ml of THF, 11.1 g (150 millimoles) of tert-butanol and 1.39 g (200 millimoles) of metallic lithium were added to a flask in that order at room temperature, followed by stirring for 30 minutes. The mixture was further refluxed for an hour. After the reaction, 10 ml of methanol was added for decomposing the excess lithium. The resulting mixture was poured into 100 ml of water and extracted with three 100-ml portions of n-pentane. The extract was dried over anhydrous magnesium sulfate. The subsequent distillation gave a product.

Boiling point: 138°–140° C.,
Yield: 4.53 g (74.3%),
Purity (gas chromatography): 93.8%

The $^{13}$C-NMR data for this product were in agreement with the literature data for 1-ethylnortricyclene [A. A. Bobyleva et al., Zh. Org. Khim., 13, 2085 (1977)].

$^{13}$C-NMR (CDCl$_3$, δc (intensity, multiplicity): 12.4(1,q), 16.1(1.5,d), 23.1(1,t), 24.4(0,3,s), 31.8(1,d), 34.2(2,t), 36.4(1,t).

Literature data:

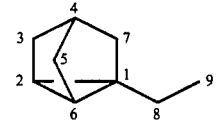

12.4(C$_9$), 16.3(C$_2$C$_6$), 23.3(C$_8$) 24.5(C$_1$), 32.0(C$_4$), 34.3(C$_3$C$_5$), 36.6(C$_7$).

Referential Example 3

1-Ethyl-3-orthomethoxyphenylnortricyclene (VII):

To a Grignard reagent prepared in a nitrogen atmosphere from 4.86 g (0.2 mole) of magnesium turnings and an equivalent amount (37.4 g) of O-bromoanisole in ether (100 ml), there was added dropwise at room temperature a solution of 40.2 g (0.2 mole) of 1-ethyl-3-bromonortricyclene (synthesized in Reference Example 2) in benzene (200 ml). Then, the ether was distilled off carefully under ordinary pressure. Thereafter, the benzene was refluxed for an hour. The reaction mixture was cooled with ice, 50 ml of 5% aqueous HCl was added dropwise, and the product was extracted with three 100-ml portions of ether. The extract was washed with one 50-ml portion of saturated aqueous sodium hydrogen carbonate and three 50-ml portions of saturated aqueous sodium chloride, and dried over magnesium sulfate. The product was distilled under reduced pressure and purified and isolated by column chromatography (Wakogel C-200). The product was a mixture of two compounds (exo and endo isomers with respect to position 3) and their contents were 84% and 16%, respectively. The following physical constants are for the mixture as it is:

Boiling point: 98.0°–100.0° C./0.02 mmHg;
Yield: 19.1 g (40.9%);
$^1$H-NMR (CDC $l_3$, TMS internal standard, $\alpha$): 7.3–6.6 (complicated multiplet, 4H, aromatic ring hydrogens), 3.7 (3H, —OCH$_3$), 3.1 (1H, Ar-C$\underline{H}$); 2.1–1.2 (complicated multiplet, 1$\underline{2H}$).
IR (liquid film, cm$^{-1}$): 3050, 2960, 2930, 2860, 1600, 1580 1490, 1460, 1440, 1240, 1110, 1050 1030, 875, 865, 785, 745, 720 $^{13}$C-NMR (CDCl$_3$, $\delta$c).
$^{13}$C-NMR data for the major product (84% content): 157.3(s), 131.0(s), 128.4(d), 126.8(d), 119.8(d), 109.5(d), 54.9(q), 44.8(d) 38.2(t), 36.0(d), 30.1(t), 25.4(s), 23.3(t), 19.6(d) 16.8(d), 12.2(q).

Referential Example 4

1-Ethyl-3-paramethoxyphenylnortricyclene (IX):

Using 2.43 g (0.1 mole) of magnesium turnings, an equivalent amount (18.7 g) of p-bromoanisole and 20.1 g of 1-ethyl-3-bromonortricyclene, the procedure of Reference Example 3 was followed to give 1-ethyl-3-paramethoxyphenylnortricyclene. The product was a mixture of two compounds (exo and endo isomers with respect to position 3: 78% and 22%). The following data were obtained using the mixture as it was:

Boiling point: 103.0°–105.0° C./0.01 mmHg;
Yield: 7.73 g (33.9%);
$^1$H-NMR (CDCl$_3$, TMS internal standard, $\delta$); 7.2–6.6 (AA'BB' system, 4H, Ar—H), 3.1 (3H, —OCH$_3$), 2.8 (1H, Ar-C$\underline{H}$), 1.8–0.8 (complicated multiplet, 9$\underline{H}$);
IR (liquid film, cm$^{-1}$): 3050, 2960, 2940, 2875, 1625, 1585 1515, 1465, 1250, 1180, 1105, 1040, 880, 860, 830, 795, 780, 755.
$^{13}$C-NMR (CDCl$_3$, $\delta$c).
$^{13}$C-NMR data for the major product (78% content): 157.7(s), 135.0(s), 128.6(d), 113.2(d), 55.2(q) 49.4(d), 38.3(d), 37.8(t), 29.8(t), 26.0(s), 23.2(t), 20.0(d), 16.4(d), 12.2(q).

Referential Example 5

1-Ethyl-3-metamethoxyphenylnortricyclene (VIII):

Using 2.43 g (0.1 mole) of Mg turnings, an equivalent amount (18.7 g) of m-bromoanisole and 20.1 g of 1-ethyl-3-bromonortricyclene, the procedure of Referential Example 3 was followed to give 1-ethyl-3-metamethoxyphenylnortricyclene.
$^{13}$C-NMR (CDCl$_3$, $\delta$c): 159.3(s), 144.5(s) 128.7(d), 120.2(d), 113.7(d), 113.2(d), 110.8(q), 54.9(d), 50.3(d), 38.3(d), 30.0(t), 26.0(s), 23.2(t), 19.8(d), 16.5(d), 12.2(q).

Having now fully described this invention, it will be apparent to one of ordinary skill in the art that many changes and modifications can be made thereto without departing from the spirit or scope of the invention as set forth herein.

What is claimed as new and is intended to be secured by Letters Patent is:

1. A fragrant mixture comprising at least one cyclohexanol derivative having the formula:

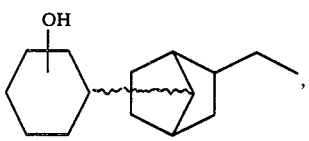

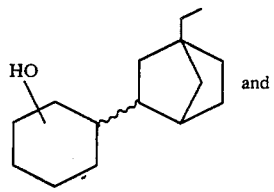

and

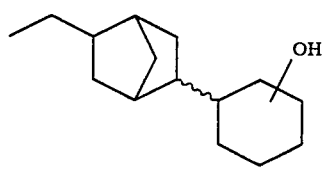

2. Soaps, detergents, shampoos, hair rinses, cosmetic products, colognes and perfumes comprising an effective amount of at least one cyclohexanol derivative having the formula:

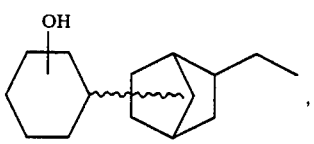

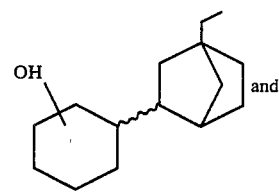

and

3. The fragrant mixture of cyclohexanol derivatives comprising at least one cyclohexanol derivative having the formula:

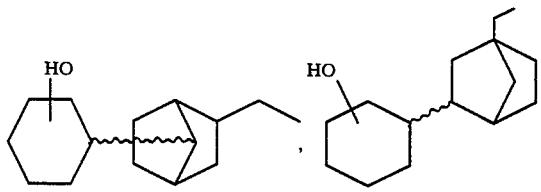

,

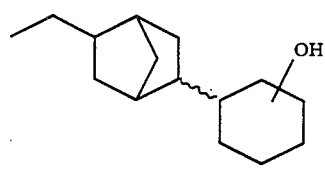

wherein the fragrant mixture is produced by condensing 2-ethylidene-5-norbornene having the formula:

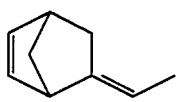

with a phenol compound of the formula:

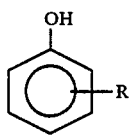

wherein R is a hydrogen atom or a hydroxy or lower alkoxy group, in the presence of a Friedel-Crafts catalyst and a suitable solvent; and hydrogenating the condensation product in the presence of a metal catalyst selected from the group consisting of Raney-nickel, nickel-on-diatomaceous earth, Raney-cobalt, platinum, rhodium, ruthenium, ruthenium-on-active carbon or palladium.

4. The fragrant mixture as in claim 3, wherein the phenol compound is selected from the group consisting of phenol, catechol, guaiacol, guethol and a phenol wherein R is a lower alkoxy group of from 1 to 4 carbon atoms.

5. The fragrant mixture as in claim 4, wherein the phenol compound is guaiacol.

6. The fragrant mixture as in claim 3, wherein the Friedel-Crafts catalyst is a cation exchange resin, boron trifluroride, boron trifluoride etherate, boron trifluoride-acetic acid, boron trifluoride-phosphoric acid, boron trifluoride-methanol, celite, acid clay, sulfuric acid, aluminum trichloride, zinc chloride, stannic chloride and ferric chloride.

7. The fragrant mixture as in claim 6, wherein the Friedel-Crafts catalyst is boron trifluoride or a complex thereof or sulfuric acid.

8. The fragrant mixture as in claim 3, wherein the Friedel-Crafts catalyst is used in an amount of about 0.01 to 40% by weight based on the phenol compound.

9. The fragrant mixture as in claim 3, wherein the molar ratio between the phenol compound and 2-ethylidene-5-norbornene is about 1:1 to 20:1.

10. The fragrant mixture as in claim 9, wherein the molar ratio is about 1.5:1 to 10:1.

11. The fragrant mixture as in claim 3, wherein the hydrogenation is effected in the range of about 1 atmosphere of pressure to 200 kg/cm$^2$.

12. The fragrant mixture as in claim 3, where the condensation reaction is effected at a temperature in the range of $-10°$ to $250°$ C.

13. The fragrant mixture as in claim 3, wherein said suitable solvent is a halogenated hydrocarbon.

14. The fragrant mixture as in claim 13, wherein said halogenated hydrocarbon is methylene chloride, chloroform or carbon tetrachloride.

15. The fragrant mixture as in claim 3, wherein said metal catalyst is ruthenium-on-active carbon.

* * * * *